United States Patent
Fuke et al.

(12) 
(10) Patent No.: US 6,284,897 B2
(45) Date of Patent: Sep. 4, 2001

(54) METHOD FOR CRYSTALLIZING TRYPTOPHAN

(75) Inventors: Ichiro Fuke, Kanagawa; Shuichi Endo; Seiji Funatsu, both of Saga, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/756,194

(22) Filed: Jan. 9, 2001

(30) Foreign Application Priority Data

Jan. 13, 2000 (JP) .................................................. 12-04668

(51) Int. Cl.$^7$ .................................................. C07D 209/20
(52) U.S. Cl. ........................... 548/497; 548/494; 548/496
(58) Field of Search ................................... 548/494, 496, 548/497

(56) References Cited

U.S. PATENT DOCUMENTS

| 4,675,339 | * | 6/1987 | Inoue et al. | 514/419 |
| 4,769,474 | * | 9/1988 | Miyahara et al. | 548/497 |
| 4,820,825 | * | 4/1989 | Ootani et al. | 548/496 |
| 5,057,615 | * | 10/1991 | Kono et al. | 548/497 |
| 5,070,208 | * | 12/1991 | Yarita et al. | 548/494 |

FOREIGN PATENT DOCUMENTS

| 0-410005-B1 | * | 12/1995 | (EP) . |
| 05-153988-A | * | 12/1991 | (JP) . |

OTHER PUBLICATIONS

Osinovskii, et al, 1989, Biotekhnologiya, 5(3), 338–342.*

* cited by examiner

*Primary Examiner*—Floyd D. Higel
*Assistant Examiner*—Andrea M. D'Souza
(74) *Attorney, Agent, or Firm*—Oblon, Spivak, McClelland, Maier & Neustadt, P.C.

(57) ABSTRACT

A method for the crystallization of tryptophan, comprising storing a tryptophan solution at a pH of 8 to 13 and at a temperature of room temperature to 100° C. for 0.5 hour to 1 week and then, followed by crystallization.

2 Claims, No Drawings

METHOD FOR CRYSTALLIZING TRYPTOPHAN

BACKGROUND OF THE INVENTION

1. Field of the Invention

The present invention relates to a method for crystallizing tryptophan to obtain spherical crystals having a large particle size which are excellent in handling at separation and drying.

2. Background Art Relating to the Invention

In general, since crystals of tryptophan are in the form of fine powder and each of the crystals has a thin plate-like shape, there are problems that the crystals are difficult to flow or precipitate in slurry conditions, and furthermore, it is difficult to handle them at solid-liquid separation or drying after the separation. Therefore, as crystals of tryptophan, it is desirable to obtain spherical crystals having a large particle size. For that purpose, in methods for crystallizing tryptophan from a solution of water or a mixed solvent of water and an organic solvent, conditions, such as a temperature, a pH, a composition of solvents and the like, are controlled (e.g., JP-A-59-39857) or a third substance is added (e.g., JP-B-5-76463 and WO 90/09372) to control the particle size and the crystal form.

Among these methods, the method in which the operating conditions are improved achieves only slight enlargement of the particle size while maintaining the shape, and cannot improve the thin plate-like shape of tryptophan crystals. Also, the method in which a third substance is added can be expected to afford larger effects on both of the particle size and the shape than the method in which the operating conditions are improved. However, in the industrial operation, an additional apparatus and step for adding the third substance are newly required, so that there are problems that not only the method is economically disadvantageous but also complicated steps are required.

SUMMARY OF THE INVENTION

An object of the present invention is to provide a method for crystallizing tryptophan in which at least one of the above defects is improved based on the chemical properties possessed by tryptophan per se.

According to the present invention, the above problems are solved, and tryptophan is crystallized by storing a tryptophan solution under alkaline conditions at room temperature or higher within a definite period of time, followed by crystallization, so that at least one of (1) tryptophan crystals having a large particle size and (2) tryptophan crystals having a spherical shape is obtained.

Specifically, the present invention relates to a method for crystallizing tryptophan, comprising storing a tryptophan solution at a pH of 8 to 13 and at a temperature of room temperature to 100° C. for 0.5 hour to 1 week, followed by crystallization.

DETAILED DESCRIPTION OF THE INVENTION

In the present invention, the room temperature is not particularly limited so long as it is a temperature at which chemical experimentation is generally carried out, and it is preferably 4° C. or higher.

Preferred conditions for the storage are shown in Table 1. When the crystallization is carried out at the pH, temperature and storage period ranges according to Table 1, effective change can be observed at the resulting crystals, and tryptophan is hardly chemically decomposed. Furthermore, when the temperature is low, a long storage period is necessary, while when the temperature is high, the effect can be obtained for a relatively short period. Among the conditions, the pH, temperature, and storage period are preferably 9.5 to 10.5, 40 to 60° C., and 1 to 2 days, respectively, in view of easy operation.

TABLE 1

| pH | Temperature | Period |
| --- | --- | --- |
| 8–13 | 30–80 ° C. | 1 hour to 1 week |
| 8–13 | 60–100 ° C. | 0.5 hour to 2 hours |

As a result that the crystallization is carried out after the storage under such conditions, (1) tryptophan crystals having a particle size as large as several hundred $\mu$m to several mm are obtained and/or (2) tryptophan crystals having a spherical shape are obtained. The resulting crystals can be separated by a usual solid-liquid separating method, such as centrifugation, filtration in vacuo, or the like.

Tryptophan used in the present invention can be L-isomer or D-isomer. Examples of the tryptophan solution include a solution in which powdered tryptophan is dissolved, and a microorganism fermented liquid and an enzymatic reaction solution containing tryptophan, which can be optionally treated with, e.g., an ion-exchange resin. Examples of a solvent for dissolving tryptophan include water and a mixed solvent of water and a water-soluble organic solvent (e.g., methanol, ethanol, acetone, or the like). The pH of the solution can be adjusted by adding an alkali. The alkali used for adjusting the pH is not particularly limited, and examples thereof include sodium hydroxide, ammonia, and the like. In addition, the tryptophan concentration of the solution is also not particularly limited.

In the present invention, tryptophan is crystallized after the tryptophan solution is stored under the conditions as described above. Any method for crystallization usually used for crystallizing tryptophan can be used. Specific examples of the method for the crystallization include a method in which tryptophan is crystallized at the same time when the solution is neutralized by adding an acid; a method in which after neutralization, the solution is concentrated or cooled, or a water-soluble organic solvent (e.g., methanol, ethanol, acetone, or the like) is added thereto; and the like.

According to the present invention, as a result that a tryptophan solution is only stored, at least one of the particle size and the shape of crystals of tryptophan after crystallization can be improved. The resulting crystals of tryptophan which have been stored are more easily handled in solid-liquid separation than those which have not been stored, and have at least one characteristic of (1) a large particle size and (2) a spherical shape.

The present invention will be explained in detail with reference to Examples. However, the present invention is not limited thereto. In the following Examples, all percents are by weight, unless otherwise indicated.

Example 1

A commercial reagent of L-tryptophan was suspended in water, and the pH was adjusted to 10 with sodium hydroxide to prepare 100 ml of a 3% aqueous solution of L-tryptophan. The solution was charged into an Erlenmeyer flask, tightly sealed to prevent evaporation of water, and stored in a constant-temperature bath under stirring at 50° C. Two days thereafter, the solution was cooled to 30° C., and the pH was adjusted to 6.5 with sulfuric acid, followed by very slowly stirring, to precipitate crystals.

As a result, spherical crystals having an average particle size of 1 mm were obtained. The crystals were very easy to precipitate and were completely separated from a clear supernatant through precipitation by only standing for a short period of time. The crystals could be easily isolated by decantation. On the other hand, when the aqueous solution of L-tryptophan prepared in the same manner as described above was immediately crystallized without storage, the slurry changed to a highly viscous cloudy liquid and the crystalline layer and the supernatant layer could not be separated by only spontaneous precipitation.

Example 2

A commercial reagent of L-tryptophan was suspended in water, and the pH was adjusted to pH 12 with sodium hydroxide to prepare 100 ml of a 3% aqueous solution of L-tryptophan. The solution was charged into an Erlenmeyer flask, tightly sealed to prevent evaporation of water, and stored in a constant-temperature bath under stirring at 60° C. Five days thereafter, the solution was cooled to 30° C., and the pH was adjusted to 6.5 with sulfuric acid, followed by very slowly stirring, to precipitate crystals.

As a result, spherical crystals having an average particle size of 1 mm were obtained. The crystals were very easy to precipitate and were completely separated from a clear supernatant through precipitation by only standing for a short period of time. The crystals could be easily isolated by decantation. On the other hand, when the aqueous solution of L-tryptophan prepared in the same manner as described above was immediately crystallized without storage, the slurry changed to a highly viscous cloudy liquid and the crystalline layer and the supernatant layer could not be separated by only spontaneous precipitation.

Example 3

From the culture liquid containing L-tryptophan obtained by fermentation, microorganisms were removed with a microfiltration membrane, and the resulting liquid was decolorized with an adsorbing resin. Then, L-tryptophan was adsorbed onto a strong acidic cation-exchange resin at a pH of 2, and was eluted by adjusting the pH to 10.5 with sodium hydroxide to obtain a purified aqueous L-tryptophan solution. The aqueous solution was diluted to the concentration of 3%, 100 ml of the solution was charged into an Erlenmeyer flask, tightly sealed to prevent evaporation of water, and stored in a constant-temperature under stirring at 50° C. Two days thereafter, the solution was cooled to 30° C., and the pH was adjusted to 6.5 with hydrochloric acid, followed by very slowly stirring to precipitate crystals.

As a result, spherical crystals having an average particle size of 0.6 mm were obtained. The crystals were very easy to precipitate and were completely separated from a clear supernatant through precipitation by only standing for a short period of time. The crystals could be easily isolated by decantation.

This application is based on Japanese application No. 2000-4668 filed on Jan.13, 2000, the entire content of which is incorporated hereinto by reference.

While the invention has been described in detail and with reference to specific embodiments thereof, it will be apparent to one skill in the art that various changes and modifications can be made therein without departing from the spirit and scope thereof. All references cited herein are incorporated in their entirety.

What is claimed is:

1. A method for the crystallization of tryptophan, comprising storing a tryptophan solution at a pH of 8 to 13 and at a temperature of room temperature to 100° C. for 0.5 hour to 1 week and then, followed by crystallization.

2. The method according to claim 1, wherein the pH, temperature, and storage period are 9.5 to 10.5, 40 to 60° C., and 1 to 2 days, respectively.

* * * * *